(12) United States Patent
Moore (10) Patent No.: US 8,212,100 B2
(45) Date of Patent: Jul. 3, 2012

(54) APPARATUS, SYSTEM, AND METHOD FOR PROTECTING AND TREATING A TRAUMATIC WOUND

(75) Inventor: Michael Moore, Orem, UT (US)

(73) Assignee: Quandra Innovations International, LLC, Salt Lake City, UT (US)

( * ) Notice: Subject to any disclaimer, the term of this patent is extended or adjusted under 35 U.S.C. 154(b) by 807 days.

(21) Appl. No.: 11/834,400

(22) Filed: Aug. 6, 2007

(65) Prior Publication Data
US 2008/0033330 A1  Feb. 7, 2008

Related U.S. Application Data

(60) Provisional application No. 60/821,527, filed on Aug. 4, 2006.

(51) Int. Cl.
*A61F 13/00* (2006.01)
(52) U.S. Cl. .......................... 602/43; 602/54
(58) Field of Classification Search .............. 602/42–54; 128/888, 889
See application file for complete search history.

(56) References Cited

U.S. PATENT DOCUMENTS

| | | | |
|---|---|---|---|
| 3,367,332 A * | 2/1968 | Groves | 604/290 |
| 3,777,757 A | 12/1973 | Gray et al. | 128/278 |
| 4,465,062 A | 8/1984 | Versaggi et al. | 128/1 |
| 4,664,660 A | 5/1987 | Goldberg et al. | 604/321 |
| 4,717,382 A | 1/1988 | Clemens et al. | 604/122 |
| 5,152,757 A * | 10/1992 | Eriksson | 604/305 |
| 5,160,322 A | 11/1992 | Scheremet et al. | 604/122 |
| 5,195,977 A | 3/1993 | Pollitt | 604/122 |
| 5,263,922 A | 11/1993 | Sova et al. | 602/59 |
| 5,431,633 A | 7/1995 | Fury | 604/122 |
| 6,447,425 B1 * | 9/2002 | Keller et al. | 482/8 |
| 6,569,121 B1 | 5/2003 | Purow et al. | 604/174 |
| 6,770,063 B2 | 8/2004 | Goldberg et al. | 604/326 |

* cited by examiner

*Primary Examiner* — Michael A. Brown
(74) *Attorney, Agent, or Firm* — Kunzler Law Group (57) ABSTRACT

An apparatus, system, and method are disclosed for protection, depressurization, and treatment of a traumatic wound. The disclosed apparatus comprises a flexible patch with an elevated portion configured to accommodate multiple connectors at least one of which is configured to interface with a two-way valve.

25 Claims, 6 Drawing Sheets

APPARATUS, SYSTEM, AND METHOD FOR PROTECTING AND TREATING A TRAUMATIC WOUND

CROSS-REFERENCES TO RELATED APPLICATIONS

This application is a continuation-in-part of and claims priority to U.S. Provisional Patent Application No. 60/821,527 entitled "APPARATUS, SYSTEM AND METHOD FOR PROTECTING AND TREATING A TRAUMATIC WOUND" and filed on Aug. 4, 2006 for Michael Moore, which is incorporated herein by reference.

BACKGROUND OF THE INVENTION

1. Field of the Invention

This invention relates to care of a wound and more particularly relates to a medical trauma patch configured to enable protection, visualization, depressurization, and irrigation of a wound.

2. Description of the Related Art

Various types of wounds, notably the type defined as a sucking chest wound, generally require prompt protection and depressurization, and are rapidly fatal in the absence of such treatment. A sucking chest wound breaches the thoracic cavity so as to allow pressure equalization with the outside atmosphere and defeats the internal vacuum required for normal function of the lungs and other organs. Such wounds must be quickly sealed off from the outside atmosphere and the internal pressure must be reduced in order to restore lung and other functions. Basic first response treatment typically includes covering the wound with an impermeable material, such as a piece of plastic, and taping the covering on three of four sides, creating an opening similar to a one-way valve. The opening allows air to escape from the wound, but prevents air or other materials from entering the thoracic cavity through the wound.

For the wound to heal, more advanced treatment is typically required to keep the wound clean and cleared of accumulated fluids, coagulated blood, and other debris. The existing art includes adhesive patches equipped with a single one-way check valve for release of pressure. These devices, however, are often insufficient for wound treatment and protection because they generally fail to enable rapid depressurization of the area beneath the patch and they lack a mechanism to enable cleaning or irrigating the wound.

Furthermore, air will not spontaneously exit through the one-way valve if the inside and outside pressure are equal. However, depressurization of the wounded area may be needed to prevent the death of the patient. The traditional one-way check valves allow for the spontaneous egress of gases and some fluids, but do not allow for the controlled application of irrigation fluids or for the egress of solids such as coagulation.

Furthermore, serious puncture wounds often occur in violent and chaotic settings. Therefore, the treatment must be rapid and simple to apply to a distressed and frequently thrashing patient in distracting conditions, often with inadequate lighting. Available trauma patches typically do not provide effective mechanisms to simplify the application process, to facilitate monitoring the patient's condition, or to enable treatment of the wound without removing the covering.

From the foregoing discussion, it should be apparent that a need exists for a medical trauma patch apparatus, system, and method for protecting and treating a traumatic wound that enables simple and rapid application and facilitates covering, protecting, and depressurizing a wound. Beneficially, such an apparatus, system, and method would also facilitate observation, cleaning, and irrigation of the wound. In addition, the apparatus, system, and method may supply enhancements to the trauma patch including auxiliary lighting, one or more sensors, and an alarm to monitor and communicate patient vital signs.

SUMMARY OF THE INVENTION

The present invention has been developed in response to the present state of the art, and in particular, in response to the problems and needs in the art that have not yet been fully solved by currently available emergency treatments for traumatic wounds. Accordingly, the present invention has been developed to provide an apparatus, system, and method for treating traumatic wounds that overcome many or all of the above-discussed shortcomings in the art.

The disclosed apparatus to treat a traumatic wound comprises a flexible patch configured to cover the wound. The patch includes an elevated module manufactured of an impermeable material. In one embodiment, the elevated module comprises multiple valves designed to facilitate depressurization of the wound cavity and other care of the wound.

The apparatus may further comprise a two-way valve configured to remain in a closed position unless held open by a properly configured device in certain embodiments. The two-way valve may be a luer lock, ball and spring, or other automatically closing design. The valve may be designed to interface with one or more wound alleviation devices such as a syringe, a hand or automatic pump, an irrigation device, and a medication dispensing device. This capability enables an operator to depressurize, irrigate, and medicate the wound cavity and also to aspirate accumulations of blood and fluid as well as rinse away coagulated blood, tissue and other debris.

The apparatus may also include a one-way valve. This may be a flutter-type valve, in certain embodiments, which may be composed of a flexible material such as surgical or other tubing that is resiliently flattened at the distal end to allow for the escape but not the entry of air or other gases. Any or all of the flexible patch, the elevated module, and the valves may be transparent to allow a clear view of the wound during application of the patch and subsequent treatment.

The elevated module containing the valve connectors may be molded in a single piece with the flexible patch. Alternatively, the valve connectors may be permanently attached in an air-tight seal. In certain embodiments, the elevated module may be removably attached in an air-tight seal by means of threads, a friction fit, or other device. Consequently, the elevated module may be removed to accommodate cleaning of the module and valves as well as cleaning and other care of the wound.

One embodiment of the disclosed invention includes a light source, which may be a light emitting diode or other small, cool, light source with a low power requirement. The light source may be used to illuminate the wound area for application of the patch in dark or low light conditions. A further embodiment may include a sensor to monitor patient vital signs. Such signs may include but not be limited to wound cavity pressure, blood pressure, temperature, pulse, and respiration rate. The light source may be coupled to the sensor in such a manner as to indicate a change or dangerous threshold level for the vital signs. This feature conveys an important benefit where a limited staff cares for multiple patients in potentially critical conditions, and rapid response to vital sign changes may determine the difference between life and death of the patient.

The flexible patch may also include an adhesive border on the surface opposite the elevated module in order to easily seal the patch over the wound. A removable backing may protect the adhesive border and the underside of the patch, including the interior cavity of the elevated module.

The present invention also discloses a system for the treatment of a traumatic wound. In addition to the flexible patch, elevated module, and various optional connectors, valves, adhesive backing, light source, sensor(s), removable elevated module and other refinements discussed above, the system may also include one or more wound alleviation modules configured to interface with the two-way valve. These may comprise, in certain embodiments, a syringe, a hand or automatic pump, an irrigation unit, and a medication dispensing device. The use of such modules facilitates the maintenance of viable pressures within the wound cavity, as well as cleaning, irrigating, and medicating the wound. In a further embodiment, the system may include a suction seal designed to cover, seal, and protect the elevation module interface of the flexible patch during removal of the elevated module.

A method for the treatment of wounds is disclosed in which a medical trauma patch as disclosed above, a two-way valve, and a depressurization module are provided. In one embodiment the operator identifies the type of wound, removes the backing from the adhesive surface of the flexible patch, applies the medical trauma patch to the wound, connects the depressurization module to the two-way valve and depressurizes the wound cavity.

The medical trauma patch provided may also include a light source, and the operator may use the light to assist in application of the patch. One or more sensors may also be provided such that the operator may monitor patient vital signs. In a further embodiment, the operator may employ the light source as a patient condition alert.

Additionally, the operator may couple a wound alleviation module to the two-way valve and aspirate, irrigate, clean, dry, and medicate the wound. The operator may also couple a fiber optic viewing device to the two-way value in order to view the wound and associated bodily cavities. In a further embodiment, the elevated module provided may be removably attached to the medical trauma patch by an air-tight seal. In this case, the operator may remove the elevated module to treat the wound directly. The operator may also protect the wound by placing the suction cover over the module connection, and clean the elevated module or replace it with a new elevated module. Subsequently, the operator may remove the suction seal and reattach the elevated module.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to give a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
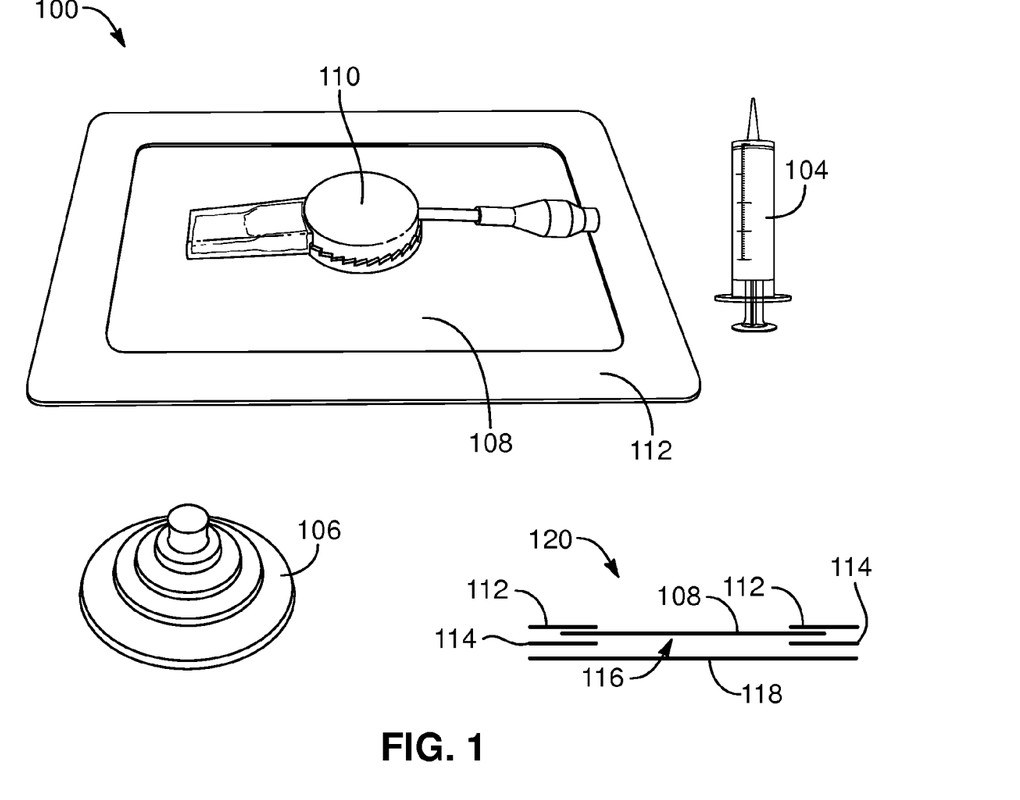
FIG. 1 is a perspective view illustrating one embodiment of a system for protecting and treating a traumatic wound in accordance with the present invention.

FIG. 1 depicts one embodiment of a wound care system 100 in accordance with the present invention. The wound care system 100, as depicted, includes a medical trauma patch 102, a wound alleviation module 104, and a suction seal 106. The wound care system 100 provides protection for a traumatic wound, in particular a chest wound that breaches the thoracic cavity. In certain embodiments, the wound care system 100 may be specifically suited to treating pneumothorax (collection of air in the pleural cavity), haemothorax (blood in the pleural cavity), and tension pneumothorax (blockage formed in the wound preventing air from leaving the pleural cavity). In addition, the wound care system 100 facilitates treating the wound while covered by the medical trauma patch 102.

The medical trauma patch 102 may include a flexible base 108 with an elevated module 110. The flexible base 108 may be made from an impermeable material, such as plastic, acetate, or the like. In certain embodiments, the material meets medical criteria and may be hypoallergenic. In addition, the material may be pliable and configured to flex around a patient's chest or the like. In the depicted embodiment, the flexible base 108 is formed into a thin film that covers the area surrounding the wound. The base 108 as well as the elevated module 110 may be transparent to enable viewing and treating the area beneath the medical trauma patch 102. In alternative embodiments, the base 108 and/or the elevated module 110 may be translucent or opaque. Given by way of example, the base 108, in one embodiment, is about five inches by seven inches.

A border 112 may circumscribe or frame the base 108 to create an adhesive seal around the medical trauma patch 102. In certain embodiments, the border 112 may be two-ply. In the depicted embodiment, the edges of the flexible base 108 are partially sandwiched between the upper border 112 and a lower adhesive element 114 to render the base 108 impervious to liquids above and/or beneath the medical trauma patch 102.

Side view 120 illustrates one embodiment of the border 112 sealing the edges of the base 108. The adhesive element 114 may be secured around the edges of the bottom side of the base 108 to adhere the medical trauma patch 102 to the patient's skin. The adhesive agent may be configured to bond to moist skin and may be similar to adhesives used in conjunction with medical bandages as is known in the art. In one embodiment, the adhesive element 114 is similar to double-sided tape and has an adhesive agent covering both the top and the bottom sides. Thus, the base 108 may be secured to the adhesive element 114, and subsequently to the patient's skin.

The upper border 112 may further include an adhesive on the bottom side to enable securing the border 112 to the base 108 and adhesive element 114, thereby forming an air-tight, liquid-tight seal around the perimeter of the base 108. In certain embodiments, the border 112 and adhesive element 114 facilitate sealing off the area 116 beneath the base 108 from the outside atmosphere and from any impurities or microorganisms that could adversely affect the wounded area. Given by way of example, the border 112 may be approximately 0.75 inches wide in certain embodiments.

Before usage, a covering 118 or protective membrane may be removably secured to the adhesive element 114 to cover the bottom side of the base 108, to protect the adhesive and to preserve the sanitation of the medical trauma patch 102, as is known in the art for packaging sterile bandages. The covering 118 may thereby be removed before applying the medical trauma patch 102 to the patient's skin.

Consequently, the medical trauma patch 102 may be easily applied to a traumatic wound by removing the covering 118, looking through the transparent base 108 to center the trauma patch 102 over the wound, and pressing on the border 112 to bond the adhesive to the skin and to seal off the area 116 beneath the patch 102. The base 108 not only provides an anchoring device for the elevated module 110 but also creates an impermeable seal against liquids, gases, and solid materials.

Figure 2:
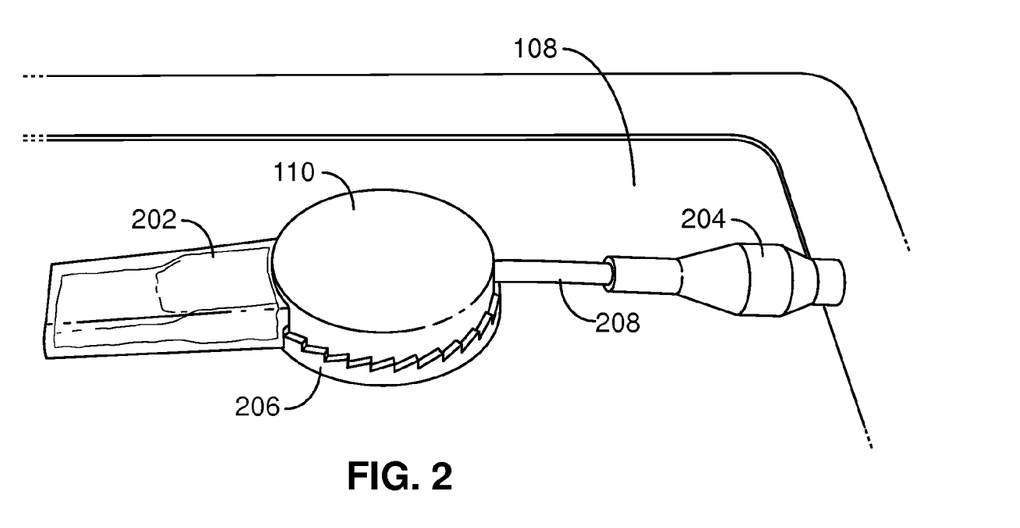
FIG. 2 is a perspective view illustrating one embodiment of an elevated module in accordance with the present invention.

FIG. 2 illustrates in greater detail one embodiment of the elevated module 110. The elevated module 110 provides an impermeable membrane and enclosure for a treatment space formed between the wound and the trauma patch 102. In addition, a plurality of connectors may be attached to the elevated module 110 to enable treatment of the wound. In one embodiment, the connectors comprise a one-way valve 202 and a two-way valve 204, which will be discussed in greater detail with respect to FIGS. 4-8.

In one embodiment, the elevated module 110 comprises an aperture in the base 108 covered by an external cavity. The external cavity may be integral to the base 108 and may be made from injection molded plastic, in certain embodiments, to provide continuity and a sure seal. Alternatively, the external cavity may be removable and/or permanently attached to the base 108 with an impermeable seal. In one embodiment, the external cavity comprises threads, enabling the operator to unscrew the external cavity. In yet another embodiment, the external cavity may be attached with a friction fit. A lip 206 for attaching the external cavity may extend from the aperture in the base 108 in certain embodiments. A rubber seal or the like may facilitate creating an impermeable seal. Given by way of example, the external cavity of the elevated module 110 may be about 1.25 inches in diameter and about 0.625 inches high in certain embodiments.

In one embodiment, a suction seal 106 may be provided to seal the elevated module interface of the flexible trauma patch 102. The suction seal 106 may prevent air from entering the wound when the external cavity is removed. In certain embodiment, the suction seal 106 may comprise a protruding rim for engaging the lip 206. Removing the elevated module 110 may facilitate cleaning the connectors and valves 202, 204 and keeping the passages free from debris and coagulated blood.

To facilitate treating the wound in certain embodiments, an umbilical tube 208 communicates into the external cavity and is connected to the two-way valve 204. The umbilical tube may be made of surgical tubing and may be sealed to an opening in the external cavity. In addition, the umbilical tube may be sealed to an opening leading to the two-way valve 204, thereby preserving the seal of the medical trauma patch 102.

The two-way valve 204 is preferably closed until activated by a corresponding device, which may be the wound alleviation module 104 in certain embodiments. The wound alleviation module 104 may be any device suitable for introducing or removing materials from beneath the trauma patch 102 or for determining the condition of the wound. Examples of wound alleviation modules 104 may include, but are not limited to, a syringe, a hand pump, an electric pump or suction device, an irrigation device, a medication dispensing device, a fiber optic or other viewing device, a diagnostic machine, or the like.

Providing a blocked opening into the external cavity enables the operator to selectively irrigate the wound, introducing medicated solutions or the like into the external cavity without exposing the wound to the atmosphere. In addition, the operator may selectively aspirate excess blood, liquid, air, or the like. Beneficially, the two-way valve 204 facilitates quickly relieving pressure build-up within the thoracic cavity.

Generally, trauma patches 102 provide a one-way valve 202 for enabling air or other materials to pass out of the wound while blocking air from entering. A single valve, however, may become clogged with coagulated materials or the like. Furthermore, the excess air may not be expelled by the wound.

By providing an additional two-way valve 204, the present invention enables the operator to treat the wound more quickly and effectively. Wound aspiration may be expedited, and coagulation and material build-up may be easily irrigated and/or removed. In addition, the transparent quality of the trauma patch embodiment 102 enables the operator to easily monitor the wound and any applied treatments.

Figure 3:
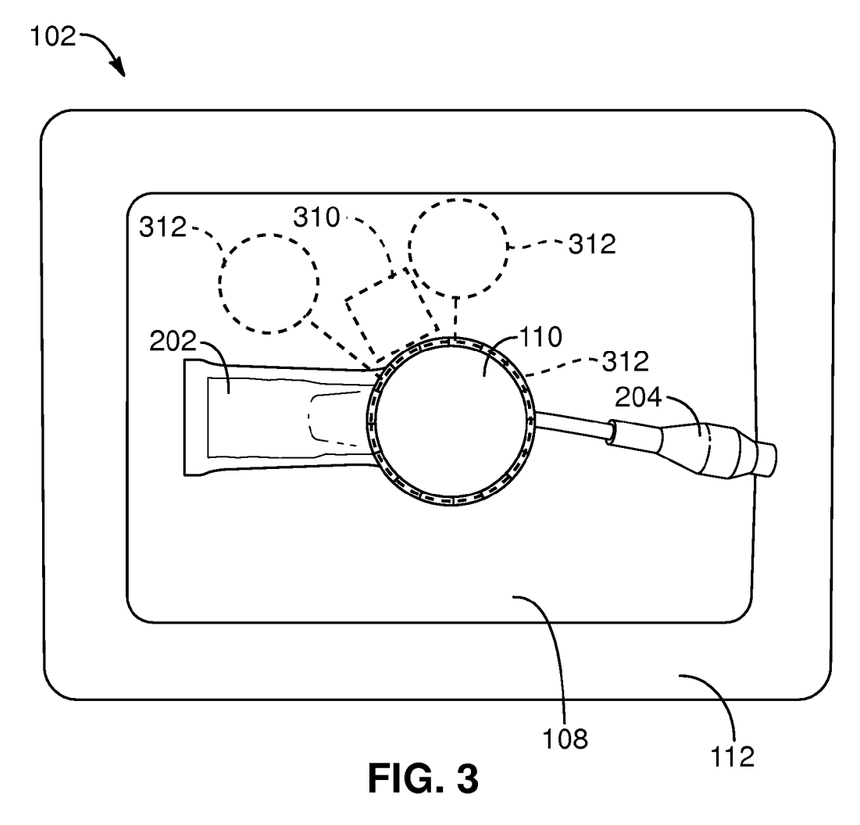
FIG. 3 is a plan view illustrating one embodiment of a medical trauma patch with sensors and a light source in accordance with the present invention.

FIG. 3 illustrates an alternative embodiment of the medical trauma patch 102 in accordance with the present invention. The trauma patch 102 further includes a light source 310 and multiple sensors 312. The light source 310 facilitates viewing the wound and may further enable the operator to apply the trauma patch 102 in low-light conditions. In a further embodiment, the light source 310 may be used to signal or notify an attendant of the patient's condition. For example, the lighted trauma patch 102 may signify a covered sucking chest wound. In one embodiment, the light source 310 may be color-coded to signify different conditions.

Beneficially, the light source 310 may be employed in an emergency situation when several patients are being treated by a limited number of staff. Chest wounds and other severe injuries can occur en masse on the battlefield or in a natural disaster. In such a condition, the light source 310 may be an indicator of the severity of the wound and the need for monitoring.

In one embodiment, the light source 310 is relatively small and requires a minimal amount of energy. An LED (Light Emitting Diode) may be suitable for such an application and may be powered by a small battery or the like. The light source 310 may be disposed on top of the trauma patch 102, in certain embodiments, and may direct the light toward the elevated module 110. Alternatively, the light source 310 may be integral to the elevated module 110 and/or the base 108. A switch may activate the light source 310 in one embodiment. In a further embodiment, the light source 310 is coupled to the sensors 312 and may be triggered by a sensor-activating condition or event.

The sensors 312 may facilitate monitoring patient vital signs and the condition of the wound. The sensors 312 may comprise a thermo-sensitive element, a pressure-sensitive element, a sound-sensitive element, and the like, and may be disposed along or integrated into the base 108 and/or the elevated module 110. Vital sign monitors or sensors 312 known in the art may be incorporated into the trauma patch 102 of the present invention. In certain embodiments, one or more sensors 312 may be coupled to a transmitter to wirelessly communicate vital sign statistics or the like to a remote device. Alternatively, a display unit (not shown) may be coupled to the trauma parch 102 to display vital sign statistics and/or a sensor-triggering event. In addition, an alarm or the like may be coupled to the sensors 312 and/or to a communicating device (not shown). The sensors 312 simplify treating and monitoring a traumatic wound.

Figure 4:
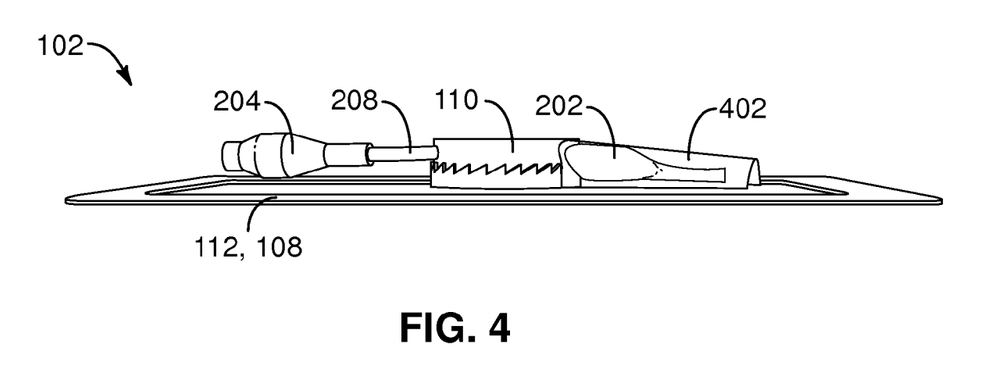
FIG. 4 is side view illustrating one embodiment of a medical trauma patch in accordance with the present invention.

FIG. 4 illustrates a side view of the medical trauma patch 102 with the elevated module 110. In the depicted embodiment, the umbilical tube 108 connecting the two-way valve 204 to the elevated module 110 is diametrically opposed to the one-way valve 202. Such an arrangement may facilitate cleaning the one-way valve 202 as injected liquids or the like may reach the one-way valve 202.

The one-way valve 202 illustrated in the depicted embodiment comprises an opening in the external cavity and a flexible tube molded around the opening. The tube, which may be made of surgical rubber, acrylic rubber, pliable plastic, or the like, extends from the opening and is flattened at the distal end to form a closure, or a flutter valve. The inside diameter of the tube may be configured to allow a certain volume of air or material to escape from the elevated module 110. However, the flat closure or flutter valve prevents air other materials from entering the elevated module 110 and subsequently the wound.

A molded guard 402 may be formed around the one-way valve 202 to protect the tube and to prevent any movement that may disturb or damage the closure or the tube. The guard 402 may be made of injection molded plastic in certain embodiments. Of course, other types of one-way valves 202 connected to the elevated module 110 are within the scope of the invention.

Figure 5:
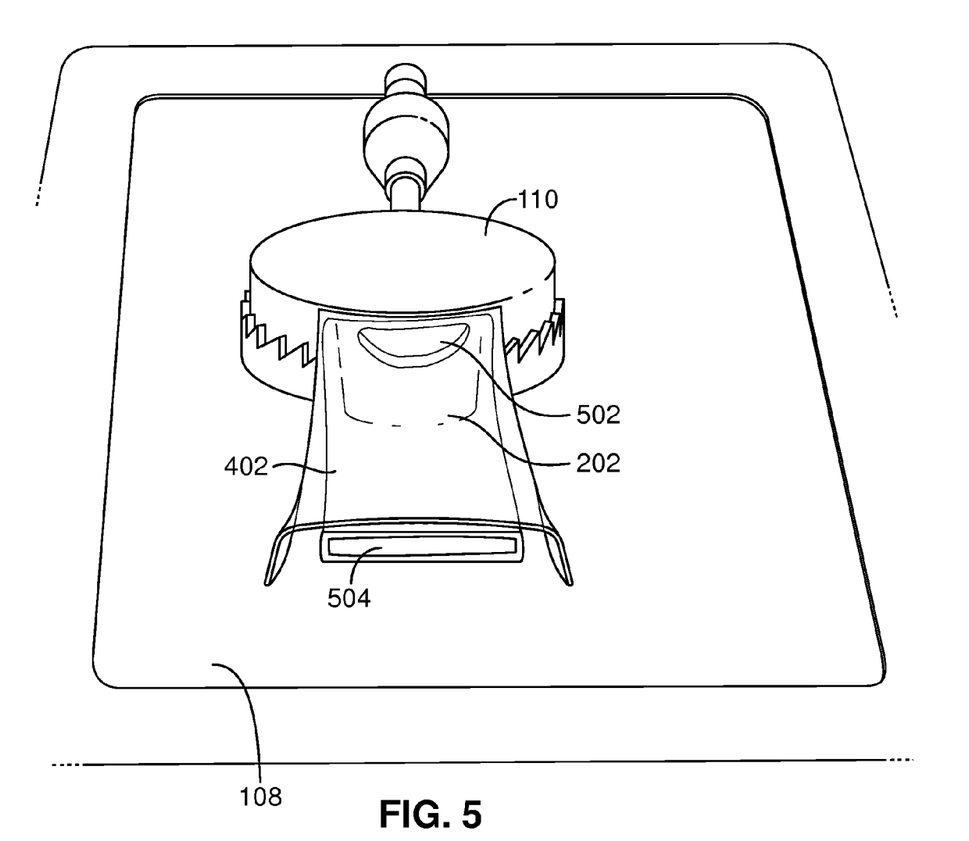
FIG. 5 is a perspective view illustrating one embodiment of a one-way valve in accordance with the present invention.
Figure 6:
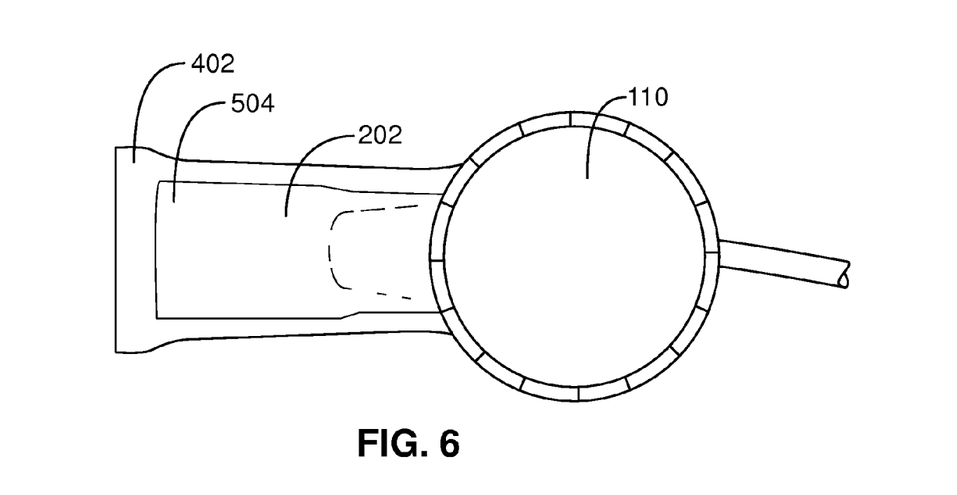
FIG. 6 is a plan view illustrating the one-way valve illustrated in FIG. 5.

FIGS. 5 and 6 are alternative views of the one-way valve 202 and illustrate the opening 502 in the elevated cavity and the closure 504 at the distal end of the tube. In addition, the guard 402 is illustrated extending over the tube to the base 108 of the trauma patch 102.

Figure 7:
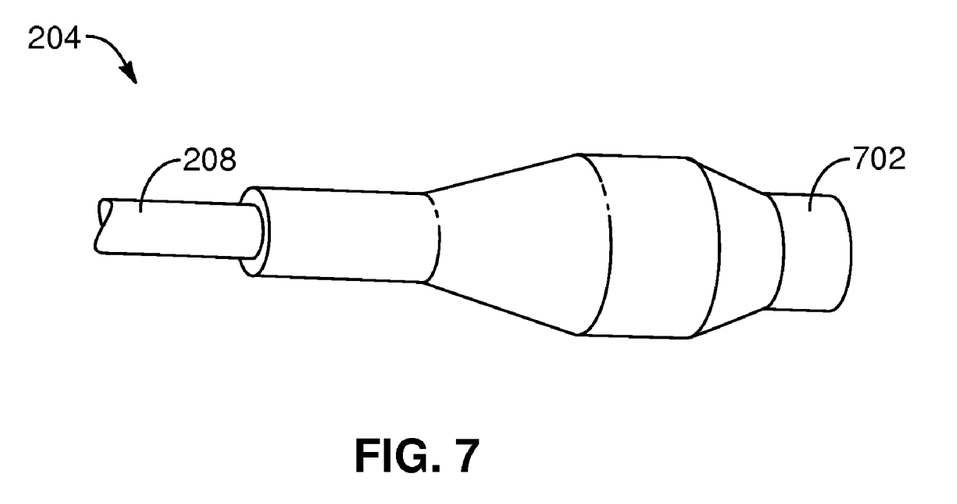
FIG. 7 is a perspective view illustrating one embodiment of a two-way valve in accordance with the present invention.

FIG. 7 illustrates in greater detail one embodiment of the two-way valve 204 molded to the umbilical tube. The two-way valve 204 may comprise a friction fit connector 702 or the like to connect a wound alleviation module 104 to the elevation module 110 as discussed above. In the depicted embodiment, the valve 204 is naturally closed until it is opened with a corresponding device, such as the tip of a syringe, for example. In one embodiment, the two-way valve 204 comprises a ball and spring valve. Alternatively, the two-way valve 204 may comprise a luer lock valve and/or connector.

Figure 8:
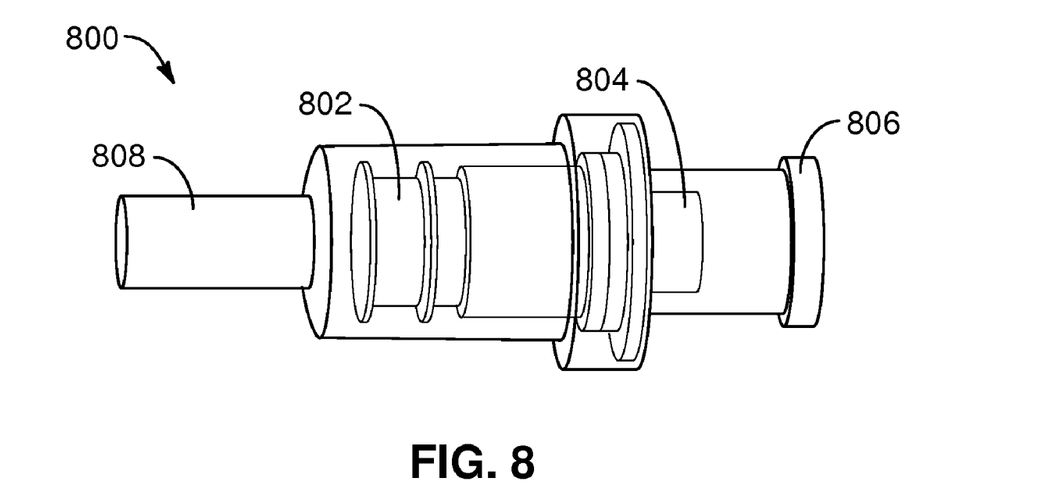
FIG. 8 is a perspective view illustrating one embodiment of a luer lock valve.

FIG. 8 illustrates one embodiment of a luer lock valve 800 that is commonly used to regulate the flow of liquids in medical devices such as syringes, IV tubes, or the like. A plug 802 prevents the inadvertent flow of the liquid. A stem 804 disposed within an elongated body 806 regulates the plug 802, and a male luer adapter 808 facilitates connecting the valve 700 to a corresponding device. Regulating the flow enables the operator to easily transfer liquids or the like between devices without causing leaks or messes to clean up. In certain embodiments, a luer lock valve 700 coupled to the elevated module 110 through the umbilical tube 108 or the like may facilitate connecting the trauma patch 102 to treatment devices that are regularly used in the medical treatment field.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Additionally, the order in which a particular method occurs may or may not strictly adhere to the order of the corresponding steps shown.

Figure 9:
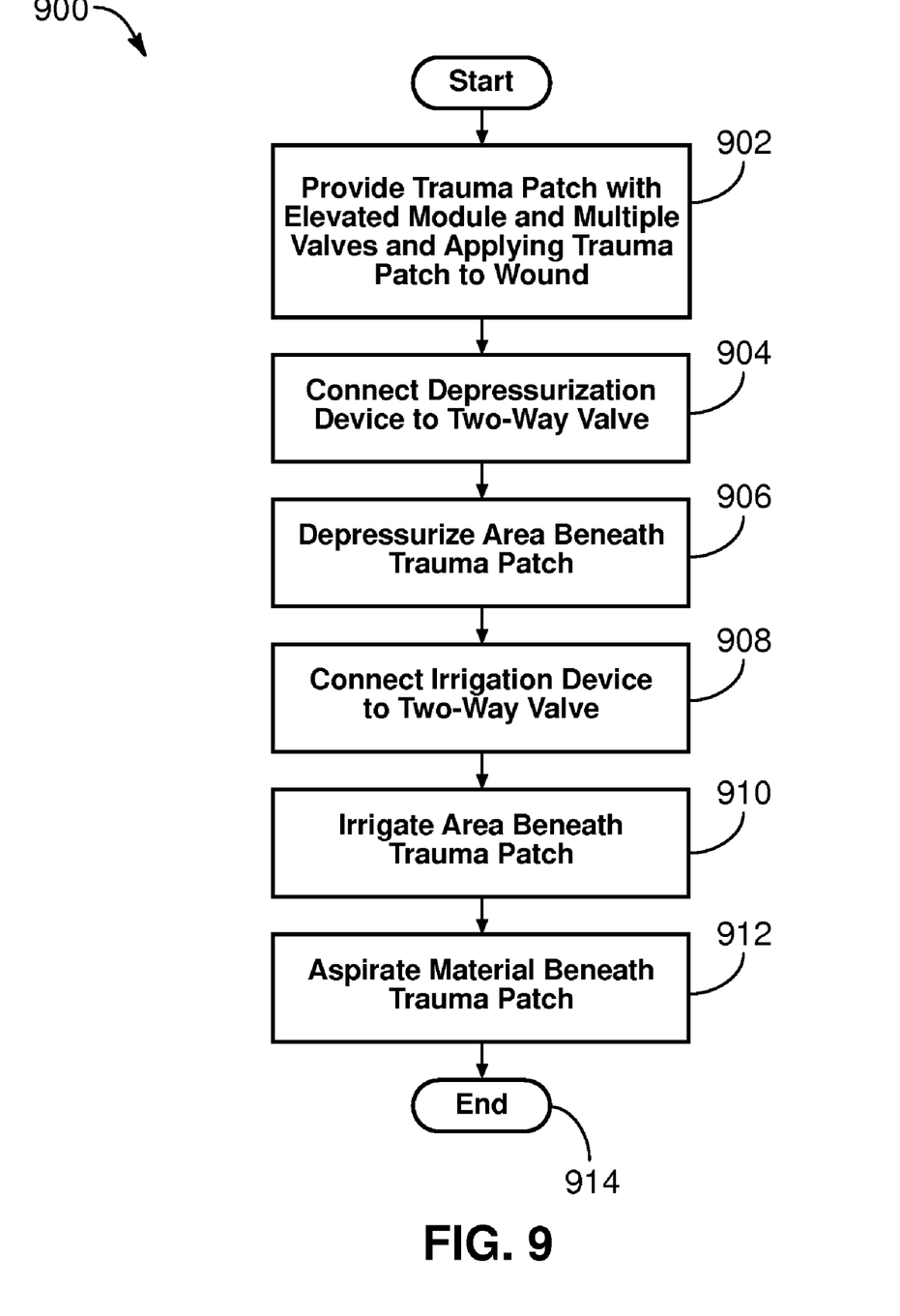
FIG. 9 is a schematic flow chart diagram illustrating one embodiment of a depressurization method for treatment of a traumatic wound in accordance with the present invention.

FIG. 9 illustrates one embodiment of a depressurization method 900 for treatment of a traumatic wound. The depressurization method 900, as depicted, comprises providing 902 a trauma patch 102 with an elevated module 110 and multiple valves 202, 204 and applying the trauma patch 102 over a traumatic wound, connecting 904 a depressurization device to the two-way valve 204, depressurizing 906 the area 116 beneath the trauma patch 102, connecting 908 an irrigation device to the two-way valve 204, irrigating 910 the area 116 beneath the trauma patch 102, and aspirating 912 the material beneath the trauma patch 102. Subsequently, the method 900 ends 914.

The method 900 enables pressure build up within the thoracic cavity from a traumatic wound such as a sucking chest wound to be depressurized quickly and efficiently. Many different suction devices, or depressurization devices, may be used to depressurize 906 the area beneath the trauma patch 102, including hand and electric pumps, syringes, or the like. The two-way valve 204 may enable irrigating 910 and/or cleaning the wound and aspirating 912 and/or drying the wound. In addition, the two-way valve 202 may facilitate medicating the wound to provide a thorough and effective treatment.

Figure 10:
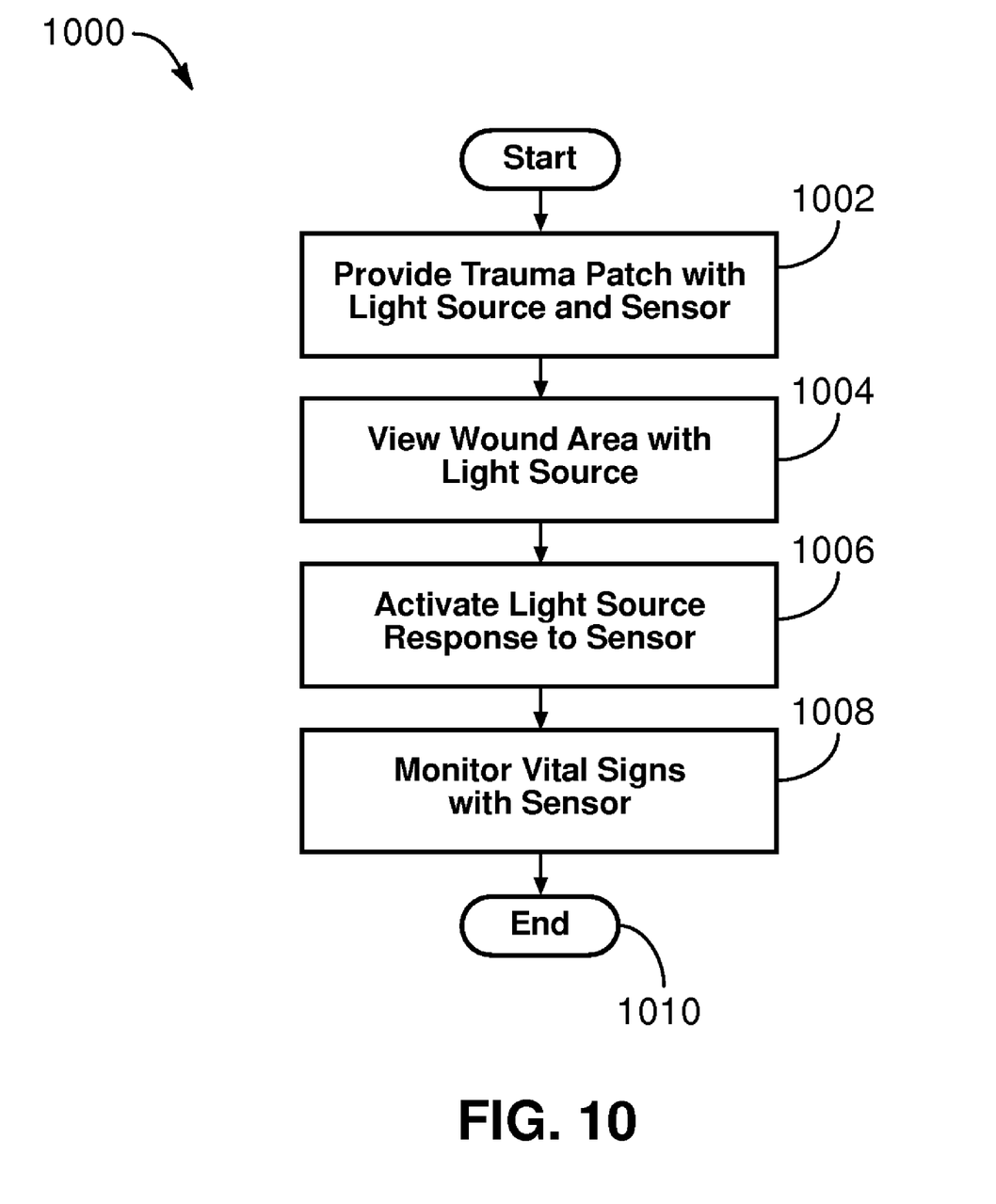
FIG. 10 is a schematic flow chart diagram illustrating one embodiment of a traumatic wound monitoring method in accordance with the present invention.

FIG. 10 illustrates one embodiment of a traumatic wound monitoring method 1000 in accordance with the present invention. The monitoring method 1002 may include providing a trauma patch 12 with a light source 310 and a sensor 312, viewing 1004 the wound area with the light source 310, activating 1006 the light source responsive to the sensor 312, and monitoring 1008 the patients vital signs with the sensor. Then, the method 1000 ends 1010.

In one embodiment, the light source 310 illuminates the wound area to facilitate applying the trauma patch 102 to the patient's skin. Once the trauma patch 102 is applied, the light source 310 may further facilitate viewing 1004 the wound area through the transparent elevated module 110 and/or base 108. Providing a clear view of the wound area may facilitate treating the wound. In certain embodiments, the light source 310 is coupled to the sensor 312 and is lighted 1006 responsive to a sensor event. For example, if the patient's heart stops or temperature fluctuates, the sensor may trigger the light source 310. Alternatively or in addition, the sensor may illuminate a digital display and/or trigger a sound alarm to notify the attending personnel. One or more sensors 312 integrated into the trauma patch 102 may facilitate monitoring 1008 the patient's vital signs.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus to treat a traumatic wound, the apparatus comprising:
   a flexible patch configured to cover and seal a wound;
   an elevated portion extending upward from the flexible patch, the elevated portion comprising an impermeable, transparent membrane defining an internal cavity;
   a plurality of valves extending outward from the elevated portion, wherein the at least one of the plurality of valves is a two-way valve; and
   an adhesive border on a surface of the flexible patch opposite the elevated portion, the adhesive border configured to seal the patch over the wound.

2. The apparatus of claim one, further comprising a protective membrane removably attached to the adhesive border and configured to cover and protect the surface of the patch opposite the elevated portion and the internal cavity of the elevated portion.

3. The apparatus of claim 1, wherein the two-way valve is selected from the group consisting of a luer lock valve, a ball and spring valve, and a pressure valve.

4. The apparatus of claim 1, wherein at least one of the plurality of valves is configured to receive a treatment device selected from the group consisting of a hand pump, an artificially powered pump, a syringe; an irrigation device, a medication dispensing device, a light, and a viewing device.

5. The apparatus of claim 4, wherein the viewing device comprises a fiber optic.

6. The apparatus of claim 1, further comprising a one-way valve.

7. The apparatus of claim 6, wherein the one-way valve is a flutter valve comprising a flexible tube, resiliently flattened at the distal end.

8. The apparatus of claim 7, further comprising a valve guard configured to protect the flutter valve.

9. The apparatus of claim 6, wherein at least one of the flexible patch, the one-way valve, and the two-way valve is transparent.

10. The apparatus of claim 1, wherein the elevated portion and the flexible patch function as a single unit, with the elevated portion permanently and impermeably attached to the flexible patch.

11. The apparatus of claim 1, wherein the elevated portion is removably attached to the flexible patch by means of an impermeable seal selected from the group consisting of threads, friction fit, snap fit, magnetic fit, and temporary adhesive.

12. The apparatus of claim 1, further comprising a light source configured to illuminate the application area of the patch.

13. The apparatus of claim 12, wherein the light source is a light emitting diode.

14. The apparatus of claim 12, further comprising a sensor configured to monitor patient vital signs and to trigger the light source.

15. A system for the treatment of a traumatic wound, the system comprising:
   a flexible patch configured to cover and seal a wound;
   an elevated portion extending upward from the flexible patch, the elevated portion comprising an impermeable, transparent membrane defining an internal cavity;
   a plurality of valves extending outward from the elevated portion, wherein the at least one of the plurality of valves is a two-way valve; and
   an adhesive border on a surface of the flexible patch opposite the elevated portion, the adhesive border configured to seal the patch over the wound.

16. The system of claim 15, further comprising a one-way valve configured to interface with the elevated portion.

17. The system of claim 15, further comprising a sensor configured to monitor patient vital signs and at least one of a light source and an auditory alarm and wherein the sensor is configured to trigger at least one of the light source and the auditory alarm.

18. The system of claim 15, further comprising a treatment device configured to interface with at least one of the plurality of valves, the treatment device selected from the group consisting of a syringe, a hand pump, an artificially powered pump, an irrigation device, a medication dispensing device, and a viewing device.

19. The system of claim 15, wherein the elevated portion is configured to removably interface with the flexible patch by means of an air-tight seal.

20. The system of claim 19, further comprising a suction seal configured to seal the elevated module interface of the flexible patch.

21. A method for the treatment of wounds, the method comprising:
    providing a medical trauma patch comprising a flexible patch having an adhesive backing and an elevated portion defining an internal cavity and configured with a plurality of valves, at least one of which is a two-way valve;
    providing a treatment device configured to interface with the at least one of the plurality of valves;
    applying the medical trauma patch to the wound;
    connecting the treatment device to the valve, and
    treating the area beneath the patch using an operation selected from the group consisting of depressurization, aspiration, irrigation, evacuation, drying, examination, and medication.

22. The method of claim 21, further providing a medical trauma patch comprising a sensor and at least one of a light source and an auditory alarm.

23. The method of claim 22, further comprising at least one of viewing the wound area during application by means of the light source and monitoring sensor output by means of at least one of the light source and the alarm.

24. The method of claim 21, further comprising providing a removable elevated portion and a suction seal configured to seal the elevated portion interface of the flexible patch.

25. The method of claim 24, further comprising removing the elevated module, sealing the wound with the suction seal, and performing at least one of treating the wound, cleaning the elevated module, providing a new elevated module, and removing the suction seal and replacing the elevated module.

* * * * *

UNITED STATES PATENT AND TRADEMARK OFFICE
CERTIFICATE OF CORRECTION

| | |
|---|---|
| PATENT NO. | : 8,212,100 B2 |
| APPLICATION NO. | : 11/834400 |
| DATED | : July 3, 2012 |
| INVENTOR(S) | : Michael Moore |

It is certified that error appears in the above-identified patent and that said Letters Patent is hereby corrected as shown below:

Column 8, Line 9

"prevents air other materials"---should read "prevents air or other materials"

Signed and Sealed this
Twenty-eighth Day of August, 2012

David J. Kappos
*Director of the United States Patent and Trademark Office*